United States Patent [19]

Atanassova et al.

[11] Patent Number: 4,711,956
[45] Date of Patent: Dec. 8, 1987

[54] PENICILLIN DERIVATIVES

[75] Inventors: Ivanka A. Atanassova; Marieta A. Haimova; Vesselina B Chavdarova, all of Sofia; Anton I. Nakov; Nedelcho G. Petkov, both of Razgrad; Ruska S. Avramova, Sofia, all of Bulgaria

[73] Assignee: TPO "Pharmachim", Sofia, Bulgaria

[21] Appl. No.: 756,018

[22] Filed: Jul. 17, 1985

[51] Int. Cl.[4] .................. C07D 499/76; C07D 499/46
[52] U.S. Cl. ..................................... 540/327; 540/316; 540/328; 540/330
[58] Field of Search ..................... 260/239.1; 540/327, 540/330, 316, 328

[56] References Cited

U.S. PATENT DOCUMENTS

| | | | |
|---|---|---|---|
| 4,159,268 | 6/1979 | Curran et al. | 260/239.1 |
| 4,317,774 | 3/1982 | Sassiver et al. | 260/239.1 |
| 4,320,133 | 3/1982 | Hamberger et al. | 260/239.1 X |
| 4,341,703 | 7/1982 | Sassiver et al. | 260/239.1 |
| 4,382,089 | 5/1983 | Haskell et al. | 260/239.1 X |
| 4,468,394 | 8/1984 | Machida et al. | 260/239.1 X |

FOREIGN PATENT DOCUMENTS 54-122288 9/1979 Japan .

Primary Examiner—Werren B. Lone
Assistant Examiner—Vera C. Clarke

[57] ABSTRACT

The invention relates to penicillin derivatives of Formula I, and a method of synthesis; the derivatives having high antimicrobial activity against gram-positive and gram-negative microorganisms.

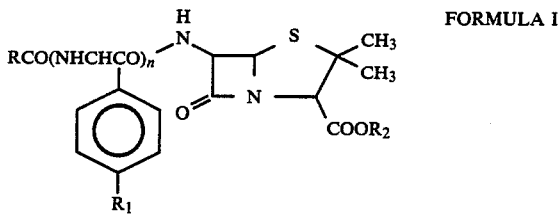

FORMULA I

R is selected from the group consisting of

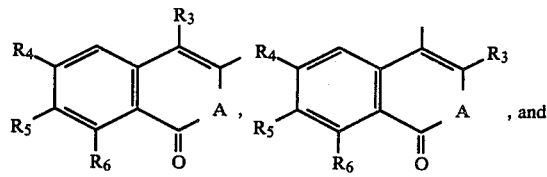

, and

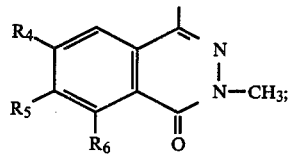

$R_1$ is selected from the group consisting of hydrogen and a hydroxyl group;
$R_2$ is selected from the group consisting of hydrogen, an alkaline metal, and a carboxy protective group;
$R_3$ is selected from the group consisting of hydrogen, a lower alkyl, and a phenyl residue;
$R_4$, $R_5$, and $R_6$ are each selected from the group consisting of hydrogen, a halogen, a lower alkyd, and a lower alkoxy group;
A is selected from the group consisting of oxygen and a N-(lower alkyl) residue; and
n is 0 or 1.

22 Claims, No Drawings

PENICILLIN DERIVATIVES

This invention relates to penicillin derivatives and a method for their preparation. The present derivatives exhibit pharmacologic activity against gram-positive and gram-negative microorganisms.

BACKGROUND OF THE INVENTION

Natural penicillin is a well-known antibiotic isolated from the mold *Penicillium luteum purpurogenum*. Many penicillins are now known, each with a different R group in the formula:

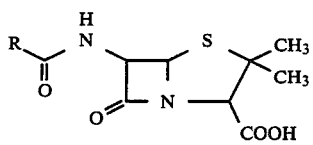

Perhaps the most widely known penicillin is benzylpenicillin (or penicillin G), in which the R group is:

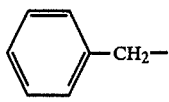

Other known derivatives include the ampicillins, in which the amino group is acylated by isocumarine-3-carboxylic acids, Bulgarian Inventors Certificate 34 532, and/or (2H)phthalazinone-4-carboxylic acids, Japan Pat. No. 7,873,593. These derivatives are active against *Ps. aeruginosa*.

SUMMARY OF THE INVENTION

The invention provides penicillin derivatives of Formula I, and a synthetic method; the derivatives having high antimicrobial activity against gram-positive and gram-negative microorganisms.

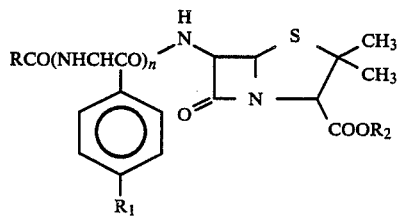

R is selected from the group consisting of

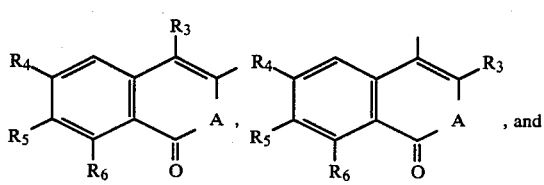, and

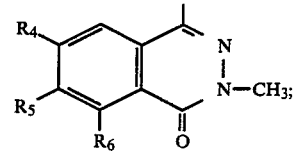

$R_1$ is selected from the group consisting of hydrogen and a hydroxyl group;
$R_2$ is selected from the group consisting of hydrogen, an alkaline metal, and a carboxy protective group;
$R_3$ is selected from the group consisting of hydrogen, a lower alkyl, a lower alkoxycarbonyl, and a phenyl residue;
$R_4$, $R_5$, and $R_6$ are each selected from the group consisting of hydrogen, a halogen, a lower alkyd, and a lower alkoxy group;
A is selected from the group consisting of an oxygen atom and a N-(lower alkyl) residue; and
n is 0 or 1.

The compounds of Formula I are synthesized by acylation of the amino group of a penamic precursor of Formula II, below, using an acylating agent of the Formula III R—CO—Z, wherein R is as defined in Formula I, and Z is a halogen atom or (—O—CO—Alk) and "Alk" is a methyl, ethyl, or tert-butyl group.

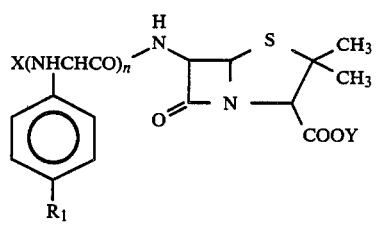

FORMULA II $R_1$ is selected from the group consisting of a hydrogen atom and a hydroxyl group;
n is 0 or 1;
X is selected from the group consisting of a hydrogen atom and a trialkylsilylic group; and
Y is selected from the group consisting of a metal, ammonium, and trialkylsilylic group.

Acylating agents of Formula III are prepared from 4-methyl-3-carboxycoumarine-7,8-dimethoxy-3-carboxyisocumarine, according to West German Pat. No. 2,448,387; from 4-methoxycarbonyl-3-carboxyisocumarine, according to S. Spassov, I. Atanassova, M. Haimova, *Org. Magn. Resonance* Vol. 22, 194 (1984); from 4-carboxyisocumarine, according to V. H. Belgaonkar, R. N. Usgaonkar, Chem. Ind., p. 954 (London, 1976); from 2-methyl-4-carboxy-1(2H)-isoquinolinone according to V. H. Belgaonkar, R. N. Usgaonkar, Tetrahedron Letters, Vol. 44, p. 3849 (1974); and from 2-methyl-4-carboxy-1(2H)-phthalazinone according to A. N. Kost, S. Foldeak, K. Grabljauskas, *Khim. Farm. Zhurnal*, 1, (3), 43 (1967).

The acylation step can be carried out according to methods previously applied to the chemistry of beta-lactamic antibiotics. G. A. Weinberg, L. N. Petruljanis, E. J. Lukevitz, *Khim. geteroziklitchnih soedinenij*, No. 2, p. 147 (1982). The acylic derivatives of Formula III are condensed with the penamic derivatives of Formula II at −20° to +20° C., in a nonaqueous or an aqueous-organic media in the presence of weak organic or inorganic bases, such as sodium bicarbonate, N,N-dimethylaniline, triethylamine, and pyridine. These bases act as hydrogen chloride binders.

In an aqueous-organic medium acceptable solvents include acetone, tetrahydrofuran, dioxan, dimethylformamide, dimethylacetamide; and dimethylsulphoxide. Nonaqueous acylation is preferably performed in organic solvents that are non-miscible with water. These include chlorinated hydrocarbons, such as chloroform and methylenechloride.

When acylation is done in a nonaqueous medium, 6-aminopenicillanic acid and its alpha-aminoderivatives are introduced to the reaction in the form of N,O-bistrialkylsilylic derivatives.

Silylation is performed in nonaqueous organic solvents, using a silylating agent preferably chosen from the group consisting of trialkylchlorsilanes, hexamethyldisilazane, N,O-bistrimethylsilyacetamide, N,N-bis-trimethylsilylcarbamide, and a combination of hexamethyldisilazane and trimethylchlorsilane.

The end-products of Formula I are isolated as metal salts by extraction from the organic solvent by a solution of sodium bicarbonate and by lyophilization or by precipitation in a suitable organic solvent such as sodium acetate or a sodium salt of diethylcapronic acid.

The compounds of Formula I can be identified and classified by their characteristic infrared and $^1$H-NMR spectroscopy profiles, their mass-spectra, and by elemental analysis. The compounds have demonstrated in vitro activity against pathogenic microorganisms, including Staph. aureus, E. coli, Ps. aeruginosa, and P. vugaris, as shown in the following table.

| STRAIN MINIMAL INHIBITING CONCENTRATION (mkg/ml) | | | | | | |
|---|---|---|---|---|---|---|
| | | Ps. aeruginosa | | | P. rettgeri | |
| COMPOUND | 2 | 14 | 184 | 185 | 158 | 159 |
| EXAMPLE 8 | — | 1.5 | 12.5 | 12.5 | 12.5 | 3.1 |
| EXAMPLE 15 | 5 | 6.25 | 12.5 | 12.5 | 12.5 | 3–1 |
| AZLOCILLIN | 5 | 12.5 | 25 | 25 | 25 | 12.5 |
| CARBENICILLIN | 5 | 25 | 100 | 100 | 6.25 | 6.25 |
| COMPOUND | Providencia 13 | P. mirabilis 15 | E. coli 171 | II-0125 | Staph. aureus 31 | |
| EXAMPLE 8 | 1.5 | 12.5 | 2.5 | 1.25 | 0.62 | |
| EXAMPLE 15 | 1.5 | 12.5 | 2.5 | 5.0 | 0.62 | |
| AZLOCILLIN | 50 | 12.5 | 10 | 10 | 0.62 | |
| CARBENICILLIN | 25 | 3.1 | 0.62 | 2.5 | 0.62 | |

DETAILED DESCRIPTION

The invention is further described with reference to a number of examples. It will be understood by those in the art that these are preferred embodiments, presented for illustrative purposes only, without serving to limit the scope of the disclosure as a whole or the appended claims.

EXAMPLE 1

Sodium salt of 6-(4'-methyl-isocumarine-3'-carboxamide-2,2-dimethyl-penam-3-carboxylic acid,

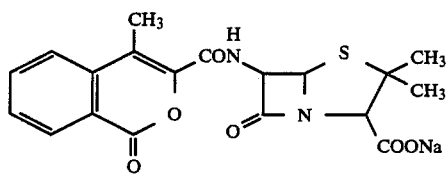

One mmole (216 mg) of 6-aminopenicillanic acid, 1.1 mmole (0.23 ml) hexamethyldisilazane, and 15.0 ml of methylene chloride are boiled to form a complete solution, followed by cooling to −5° C. One mmole (0.14 ml) of triethylamine is added, followed by portions of solid acid chloride prepared from 1 mmole (204 mg) 4-methyl-isocumarine-3-carboxylic acid and 3.0 ml thionylchloride. Cooling is discontinued and the reaction mixture is stirred for one hour at room temperature. The solvent is removed in a vacuum at 40° C. Next, 10 ml of ethylacetate are added to the residue and the mixture is again cooled to −5° C. Water (2 ml) is added, and the solution is acidified to pH=2 with concentrated hydrochloric acid. The organic sodium sulphate layer is separated and dried, and an equivalent quantity of a saturated alcoholic solution of sodium acetate is added. The two layers are separated and after drying (sodium sulphate) to the organic layer equivalent quantity of saturated alcohol solution of sodium acetate is added. The sodium salt precipitate is filtered and washed with acetone.

The yield is 290 mg (68%) of the compound of the example, having a melting point of 178°-181° C. (with decomposition).

The IR spectrum (nujol, cm$^{-1}$) is: 1600 (COO$^-$); 1650 (CO, amide); 1730 (CO, lactone) with inflex at 1780 (CO, beta-lactam) and 3400 (NH).

EXAMPLES 2-7

These exemplary compounds were synthesized from 216 mg of aminopenicillanic acid according to the method of Example 1, with the results as set forth in TABLE 1.

EXAMPLES 8-17

These exemplary compounds were synthesized from 1 mmole (349 mg) of ampicillin according to the method of Example 1, with the results as set forth in TABLE 2.

TABLE 1

| Example Nr. | Compound | Yield % | M.P. °C.(dec.) | IR-Spectrum (nujol,cm$^{-1}$) |
|---|---|---|---|---|
| 2 | Sodium salt of 6-(7',8'-dimetoxy-isocumarine-3'-carboxamide)2,2-dimethyl-penam-3-carboxylic acid | 64 | 212-214 | 1560(COO$^-$),1690(CO, amide),1770-broad (CO,lacton,CO,beta-lactam), 3300 (NH) |
| 3 | Sodium salt of 6-(4'-metoxycarbonyl-3'carboxamide)-2,2-dimethyl-penam-3-carboxylic acid | 61 | 176-178 | 1580(COO$^-$),1650(CO, amide),1700(CO,ester), 1760 broad with inflex 1780(CO,lactone,CO,beta-lactam), 3400 (NH) |
| 4 | Sodium salt of 6-(isocumarine-4'-carboxamide)-2,2-dimethyl-penam-3-carboxylic acid | 59 | 195-199 | 1590(COO$^-$),1660(CO, amide),1720(CO,lactone) 1780(CO,beta-lactam), 3400 (NH) |
| 5 | Sodium salt of 6-(3'-methyl-isocumarine-4'-carboxamide)-2,2-dimethyl-penam-3-carboxylic acid | 65 | 220-222 | 1580(COO$^-$,1660-broad (CO,amide),1750-broad |

TABLE 1-continued

| Example Nr. | Compound | Yield % | M.P. °C.(dec.) | IR-Spectrum (nujol, cm⁻¹) |
|---|---|---|---|---|
| | [structure: CONH-penam with isocoumarin-type fused system, CH3, COONa] | | | (CO,lactone,CO,beta-lactam, 3400 (NH) |
| 6 | Sodium salt of 6-/2'-methyl-1'(2H)—isoquinolinone-4'-carboxamide/-2,2-dimethyl-penam-3-carboxylic acid [structure] | 61 | 218–220 | 1600(COO⁻),1660(CO, amide),1780(CO,beta-lactam), 3400 (NH) |
| 7 | Sodium salt of 6-[2'-methyl-1'(2'H)—phtalazinone-4'-carboxamide]-2,2-dimethyl-penam-3-carboxylic acid [structure] | 64 | 205–210 | 1600(COO⁻),1640 and 1660(CO,amide),1780 (CO,beta-lactam), 3400 (NH) |

TABLE 2

| Example Nr. | Compound | Yield % | M.P. °C. (dec.) | IR-Spectrum (Nujol, cm⁻¹) |
|---|---|---|---|---|
| 8 | Sodium salt of 6-[N—(4'-methyl)-isocumarine-3'-carbonyl)-2R—2-aminophenylacetamide]-2,2-dimethyl-penam-3-carboxylic acid [structure] | 58 | 134–138 | 1600(COO⁻), 1660(CO, amide), 1730(CO, lactone), 1780(CO, beta-lactam), 3300 (NH); iodometric activity 1023,96 U/mg (quantitative content-96,1%) |
| 9 | Sodium salt of 6-[N—(7',8'-di metoxy-isocumarine-3'-carbonyl)-2R—2-aminophenylacetamide]-2,2-dimethyl-penam-3-carboxylic acid [structure] | 60 | 228–230 | 1570(COO⁻), 1680(CO, amide), 1780(broad, CO, lactone and CO, beta-lactam), 3400 (NH) Iodometric activity 860,72 U/mg (quantitative content) 87,5%) |
| 10 | Sodium salt of 6-[N—(4'-metoxy-carbonyl-isocumarine-3'-carbonyl)-2R—2-aminophenyl-acetamido]-2,2-dimethyl-penam-3-carboxylic acid | 58 | 196–200 | 1580(COO⁻), 1680(broad CO, amide), 1750-broad, inflex at 1780(CO, ester, lactone and beta-lactam) 3340 (NH). |

TABLE 2-continued

| Ex. ample Nr. | Compound | Yield % | M.P. °C. (dec.) | IR-Spectrum (Nujol, cm$^{-1}$) |
|---|---|---|---|---|
| | (structure with COOCH$_3$, CONHCHCONH-C$_6$H$_5$, penam with S, CH$_3$, CH$_3$, COONa) | | | iodometric activity 905,24 U/mg (quantitative content 91,7%) |
| 11 | Sodium salt of 6-[N—(isocumarine-4'-carbonyl)-2R—2-aminophenylacetamide]-2,2-dimethyl-penam-3-carboxylic acid | 60 | 220–224 | 1600(COO$^-$), 1660(CO, amide), 1780(CO, beta-lactam) 3300 (NH) |
| 12 | Sodium salt of 6-[N—(3'-methyl-isocumarine-4'-carbonyl)-2R—2-aminophenylacetamide]-2,2-dimethyl-penam-3-carboxylic acid | 58 | 186–190 | 1590(COO$^-$), 1670(CO, 1750-broad, inflex at 1780(CO, lactone, CO, beta-lactam), 3400 (NH) |
| 13 | Sodium salt of 6-[N—(2'-methyl-1'/2'H/—isoquinolinone-4'-carbonyl)-2R—2-aminophenylacetamide]-2,2-dimethyl-penam-3-carboxylic acid | 61 | 235–240 | 1590(COO$^-$), 1660(CO, amide), 1770(CO, beta-lactam), 3400 (NH) |
| 14 | Sodium salt of 6-[N—(2-methyl-1'/2'H/—phtalazinone-4'-carbonyl/-2R—2-aminiphenylacetamide]-2,2-dimethyl-penam-3-carboxylic acid | 58 | 218–222 | 1590(COO$^-$), 1680-CO, amide, 1780 (CO, beta-lactam), 3400 (NH) |
| 15 | Sodium salt of 6-[N—(2',4'-dimethyl-1'/2H/—isoquinolinone-3-carbonyl/-2R—2-aminiphenylacetamide]-2,2-dimethyl-penam-3-carboxylic acid | 72 | 245–248 | 1600(COO$^-$), 1650 (CO, amide), 1780 (CO, beta-lactam) 3400 (NH) iodometric activity 1009, 12 U/mg (quantitative content: 91,5%) |

TABLE 2-continued

| Ex. ample Nr. | Compound | Yield % | M.P. °C. (dec.) | IR-Spectrum (Nujol, cm$^{-1}$) |
|---|---|---|---|---|
| 16 | Sodium salt of 6-[-(4'-phenyl-isocumarine-3'carbonyl)-2R—2-aminophenylacetamide]-2,2-dimethyl-penam-3-carboxylic acid 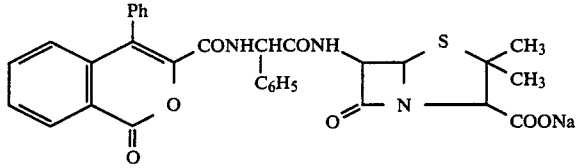 | 68 | 210–212 | 1650(CO, amide), 1710(CO, lactone), 1780(CO, beta-lactam), 3300 (NH) iodometric activity 985,55 U/mg (quantitative content: 92,9%) |
| 17 | Sodium salt of 6-/N—(2'-methyl-4'-phenyl-1'(2H)—isoquinolinone-3'-carbonyl)-2R—2-aminiphenylacetamidoI—2,2-dimethyl-penam-3-carboxylic acid 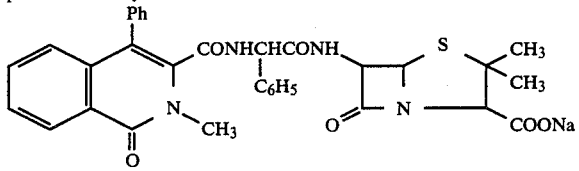 | 65 | 215–217 | 1660(CO, amide), 1780(CO, beta-lactam) 3300 (NH). Iodometric activity 938,83 U/mg (Quantitative content-96,4%). |

EXAMPLE 18

Methyl ester of 6-(4'-methyl-isocumarine-3'-carboxamide)2,2-dimethyl-penam-3-carboxylic acid,

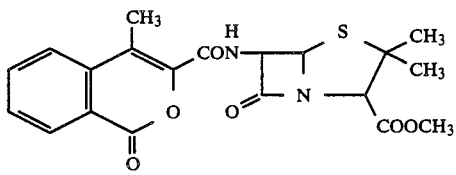

One mmole (216 mg) of 6-aminopenicillanic acid is acylated by acid chloride prepared from 1 mmole (204 mg) 4-methylisocumarine-3-carboxylic acid and the reaction mixture is treated according to the method of Example 1. An ether solution of diazomethane is added to the dried ethylacetic solution of the antibiotic. After two hours the solvent is removed in vacuo and the residue is recrystalized from isopropanol.

The yield is 260 mg (63%), with a melting point of 161°–162° C.

The IR spectrum (nujol, cm$^{-1}$) is: 1680 (CO, amide); 1730 (CO, lactone and CO, ester), 1800 (CO, beta-lactam) and 3430 (NH).

The $^1$-H-NMR spectrum is (acetone-d$_6$), 100 MHz, delta: 1.52 and 1.68 [2×3H, each s, C(CH$_3$)$_2$]; 2.64 (s, 3H, CH$_3$); 3.76 (s, 3H, OCH$_3$); 4.48 (s, 1H, 3-H); 5.6–5.9 (m, 5-H and 6-H); 7.6–8.0 (3 aromatic H); 8.0–8.3 (m, 8-H and NH).

Calculated % N=6.73; S=7.68; Found % N=6.80; S=8.01. C$_{20}$H$_{20}$N$_2$O$_6$S (416,38).

EXAMPLE 19

Methyl ester of 6-(7',8'-dimethoxy-isocumarine-3'-carboxamide)-2,2-dimethyl-penam-3-carboxylic acid,

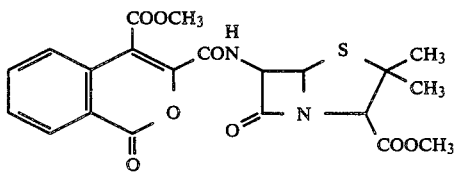

This compound is prepared according to the method of Example 18, from 1 mmole (216 mg) of 6-aminopenicillanic acid and 1 mmole (250 mg) of 7,8-dimethoxy-isocumarine-3-carboxylic acid.

The yield is 300 mg (65%), with a melting point of 83°–85° C. (from isopropanol).

The IR spectrum (chloroform, cm$^{-1}$) is: 1690 (CO, amide); 1750-broad (CO, lactone and CO, ester), 1800 (CO, beta-lactam) and 3440 (NH).

The $^1$H-NMR spectrum is (DMCO-d$_6$), 100 MHz, delta: 1.42 and 1.62 [2×3H, each s, C(CH$_3$)$_2$]; 3.68 (s, 3H, OCH$_3$); 3.76 (s, 3H, OCH$_3$); 3.86 (s, 3H, COOCH$_3$); 4.44 (s, 1H, 3-H); 5.5–5.7 (m, 2H,5-H and 6-H); 7.2–8.2 (m, 3 aromatic H); 8.6 (m, 1H, NH exchanged with D$_2$O).

Calculated % N=6.06; S=6.92; Found % N=5.50; S=6.72. C$_{21}$H$_{22}$N$_2$O$_8$S (462,40).

EXAMPLE 20

Methyl ester of 6-(4'-metoxycarbonyl-isocumarine-3'-carboxamide)-2,2-dimethyl-penam-3-carboxylic acid, prepared according to the method of Example 18, from 1 mmole (216 mg) of 4-metoxycarbonyl-isocumarine-3'-carbonic acid.

The yield is 290 mg (63%), with a melting point of 85°–87° C. (from isopropanol).

The IR spectrum (chloroform, cm$^{-1}$) is: 1680 (CO, amide); 1740 (CO, delta-lactone and CO, ester), 1790 (CO, beta-lactam) and 3400 (NH).

The $^1$H-NMR spectrum is (CDCl$_3$), 80 MHz, delta: 1.51 and 1.72 [2×3H, each s, 6H, C(CH$_3$)$_2$]; 3.78 (s, 3H, COOCH$_3$); 4.02 (s, 3H, COOCH$_3$); 4.50 (s, 1H, 3-H); 5.4–6.0 (m, 2H, 5-H and 6-H); 7.2–8.0 (m, 3 aromatic H); 8.2–8.5 (m, 1H, 8-H).

Calculated % C=54.78; N=6.09; H=4.38; Found % C=54.16; N=6.52; H=4.52. C$_{21}$H$_{20}$N$_2$O$_8$S (460,39).

EXAMPLE 21

Methyl ester of 6-isocumarine-4'-carboxamide)-2,2-dimethylpenam-3-carboxylic acid,

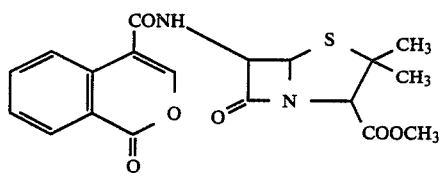

prepared according to Example 18, from 1 mmole (216 mg) of 6-aminopenicillanic acid and 1 mmole (190 mg) 4-carboxyisocumarine.

The yield is 250 mg (63%), with a melting point of 89°–92° C. (from isopropanol).

The IR spectrum (nujol, cm$^{-1}$) is: 1690 (CO, amide); 1740-broad (CO, delta-lactone and CO, ester), 1800 (CO, beta-lactam) and 3400 (NH).

The $^1$H-NMR spectrum is (acetone-d$_6$), 100 MHz, delta: 1.48 and 1.64 [2×3H, each s, C(CH$_3$)$_2$]; 3.76 (s, 3H, OCH$_3$); 4.40 (s, 1H, 3H); 5.6–5.8 (5-H, 6-H, m); 7.5–8.3 (m, 5 aromatic H and NH).

Calculated % N=6.66; S=7.61; Found % N=6.29; S=7.45. C$_{19}$H$_{18}$N$_2$O$_6$S.H$_2$O (420,37).

EXAMPLE 22

Methyl ester of 6-(3'-methyl-isocumarine-carboxamide)-2,2-dimethyl-penam-3-carboxylic acid,

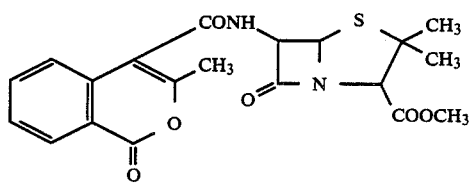

prepared according to Example 18, from 1 mmole (216 mg) of 6-aminopenicillanic acid and 1 mmole (204 mg) 3-methyl-4-carboxyisocumarine.

The yield is 250 mg (60%), with a melting point of 88°–92° C. (from isopropanol).

The IR spectrum (chloroform, cm$^{-1}$) is: 1690 (CO, amide); 1740-broad (CO, lactone and CO, ester), 1790 (CO, beta-lactam) and 3400 (NH).

The $^1$H-NMR spectrum is (acetone-d$_6$), 100 MHz, delta: 1.44 and 1.56 [2×3H, each s, C(CH$_3$)$_2$]; 2.32 (s, 3H, OCH$_3$); 3.68 (s, 3H, OCH$_3$); 4.36 (delta 1H, 3-H); 5.6–5.8 (m, 2H, 5-H and 6-H,); dd, J$_{5.6}$=4.5 Hz, dd (after exchange with D$_2$O); 7.1–8.5 (m,4 aromatic H and NH).

Calculated % N=6.73; S=7.68; Found % N=6.63; S=7.92. C$_{20}$H$_{20}$N$_2$O$_6$S (416,38).

EXAMPLE 23

Methyl ester of 6-(2'-methyl-1(2H)-isoquinolinone-4'-carboxamide)-2,2-dimethyl-penam-3-carboxylic acid,

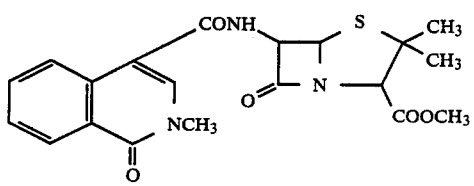

prepared according to Example 18, from 1 mmole (216 mg) of 6-aminopenicillanic acid and 1 mmole (203 mg) 2-methyl-1(2H)-isoquinolinone-4-carboxylic acid.

The yield is 245 mg (59%), with a melting point of 118°–122° C. (from isopropanol).

The IR spectrum (chloroform, cm$^{-1}$) is: 1660 (CO, amide); 1740 (CO, ester), 1790 (CO, beta-lactam) and 3400 (NH).

The $^1$H-NMR spectrum is (acetone-d$_6$), 100 MHz, delta: 1.44 and 1.60 [2×3H, each s, C(CH$_3$)$_2$]; 3.52 (s, 3H, NCH$_3$); 3.72 (s, 3H, OCH$_3$); 4.40 (s, 1H, 3-H); 5.6–5.8 (m, 2H, 5-H and 6-H); 7.3–8.4 (m, 5 aromatic H and NH).

Mass spectrum M/E: 415(M$^+$) C$_{20}$H$_{21}$N$_3$O$_5$S (415,39)

EXAMPLE 24

Methyl ester of 6-(2'-methyl-1'(2'H)-phthalazinone-4'-carboxamide)-2,2-dimethyl-penam-3-carboxylic acid,

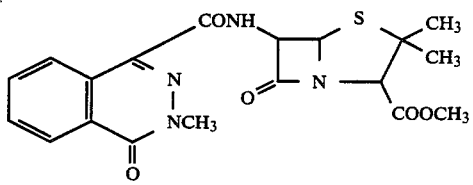

prepared according to Example 18, from 1 mmole (216 mg) of 6-aminopenicillanic acid and 1 mmole (204 mg) 2-methyl-1(2H)-phthalazinone-4-carboxylic acid.

The yield is 270 mg (65%), with a melting point of 98°–100° C. (from isopropanol).

The IR spectrum (chloroform, cm$^{-1}$) is: 1670-broad (CO, amide); 1750 (CO, ester), 1800 (CO, beta-lactam) and 3400 (NH).

The $^1$H-NMR spectrum is (acetone-d$_6$), 100 MHz, delta: 1.48 and 1.64 [2×3H, each s, C(CH$_3$)$_2$]; 3.72 (delta, 3H, NCH$_3$); 3.74 (s, 3H, OCH$_3$); 4.44 (s, 1H, 3-H); 5.6–5.8 (m, 2H, 5-H and 6-H,); J$_{5.6}$=4.5 Hz, dd (after exchange with D$_2$O); 7.6–7.8 (m, 3 aromatic H); 8.1–8.3 (m, 1H, 8-H); 8.7–8.9 (m, 1H, NH).

Calculated % N=13.46; S=7.68; Found % N=13.08; S=7.79. C$_{19}$H$_{20}$N$_4$O$_5$S (416,38).

EXAMPLES 25 TO 32

These exemplary compounds were synthesized from 1 mmole (349 mg) of ampicillin according to the method of Example 18, with the results as set forth in TABLE 3.

The ability of a number of the inventive compounds to inhibit microorganisms is shown by TABLES 4 and 5, which set forth the minimum concentration of antibiotic (in mkg/ml) necessary to inhibit *Ps. aeruginosa* 2, *P. vulgaris* 10, *Staph. aureus* 31, *P. mirabilis* 171, and *E. coli* II-0125. In general, sodium salts of the inventive compounds show a high level of in vitro activity against *staph. aureus* 31. The ampicillins derived from isocoumarin-3- or 1(2H)-isoquinoline-3-carboxylic acids also exhibit a broad spectrum of activity. Some have been found particularly adventageous for *Ps. aeruginosa*.

TABLE 3

| Example Nr. | Compound | Yield % | M.P. °C. | IR-Spectrum cm$^{-1}$ | Elemental analysis<br>+ Calculated<br>++ Found |
|---|---|---|---|---|---|
| 25 | Methyl ester of 6-/N—(4'-methyl-isocumarine-3'-carbonyl)-2R—2-aminophenylacetamide/-2,2-dimethyl-penam-3-carboxylic acid | 60 | 118–120 | (chloroform) 1660(CO,amide), 1730-broad(CO, lactone and CO, ester),1790(CO, beta-lactam), 3400 (NH) | C$_{28}$H$_{27}$N$_3$O$_7$S (549,52)<br><br>+ N 7,65<br>++ N 7,21,<br>+ S 5,82<br>++ S 6,11 |
| 26 | Methyl ester of 6-/N—(7',8'-dimetoxy-isocumarine-3'-carbonyl)-2R—2-aminophenylacetamido/-2,2-dimethyl-penam-3-carboxylic acid | 63 | 130–132 | (chloroform) 1680(CO,amide) 1740-broad (CO,ester,CO lactone), 1800-CO,beta-lactam),3440(NH) | C$_{29}$H$_{29}$N$_3$O$_9$S (595,30)<br><br>+ N 7,06 S 5,38<br>++ N 6,94 S 6,14 |
| 27 | Methyl ester of 6-[N—(4'-metoxycarbonyl-isocumarine-3'-carbonyl)-2R—2-aminophenylacetamide]-2,2-dimethyl-penam-3-carboxylic acid | 62 | 143–145 | (nujol) 1680(CO,amide) 1730-broad(CO, ester and lactone) 1790(CO,beta-lactam ,3400 (NH) | C$_{29}$H$_{27}$N$_3$O$_9$S (593,10)<br><br>+ N 7,08 S 5,39<br>++ N 7,20 S 5,54 |
| 28 | Methyl ester of 6-[N—(isocumarine-4'-carbonyl)-2R—2-aminophenylacetamide/-dimethyl-penam-3-carboxyl acid | 63 | 103–105 | (chloroform) 1680(CO,amide) 1740-broad (CO,lactone and CO,ester) 1800(CO,lactam) 3400 (NH) | C$_{27}$H$_{25}$N$_3$O$_7$S.H$_2$O (553,51)<br><br>+ N 7,59 S 5,48<br>++ N 7,29 S 5,63 |
| 29 | Methyl ester of 6-[N—(3'-methyl-isocumarine-4'-carbonyl)-2R—2-aminiphenylacetamido]-2,2-dimethyl-penam-3-carboxylic acid | 60 | 104–108 | (chloroform) 1680(CO,amide), 1740-broad (CO,lactone and CO,ester), 1790(CO,beta- | C$_{28}$H$_{27}$N$_3$O$_7$S (549,52) |

TABLE 3-continued

| Example Nr. | Compound | Yield % | M.P. °C. | IR-Spectrum cm$^{-1}$ | Elemental analysis + Calculated ++ Found |
|---|---|---|---|---|---|
| | 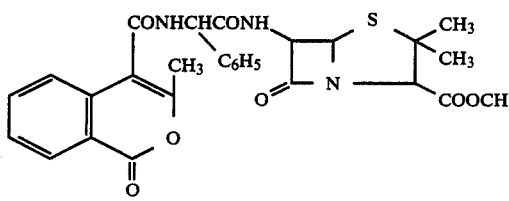 | | | lactam),3400 (NH) | + N 7,65 S 5,82<br>++ N 7,26 S 5,54 |
| 30 | Methyl ester of 6-[N—(2'-methyl-1'(2H)—isoquinolinone-4'-carbonyl/-2R—2-aminophenylacetamide]-2,2-dimethyl-penam-3-carboxylic acid | 57 | 140–143 | (nujol) 1660(CO,amide), 1740(CO,ester), 1790(CO,beta-lactam),3300 (NH) | $C_{28}H_{28}N_4O_6S$ (548,54) |
| | 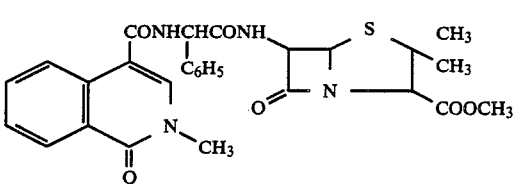 | | | | + N 10,21 S 5,84<br>++ N 9,87 S 6,13 |
| 31 | Methyl ester of 6-[N—(2'-methyl-1'/2H/—phtalazinone-4'-carbonyl)-2R—2-aminophenylacetamide]-2,2-dimethyl-penam-3-carboxylic acid | 62 | 118–120 | (chloroform) 1670-broad (CO,amide), 1740(CO,ester), 1810(CO,beta-lactam),3400(NH) | $C_{27}H_{27}N_5O_6S$ (549,53)<br><br>Mass spectrum - M/E: 549(M$^+$) |
| | 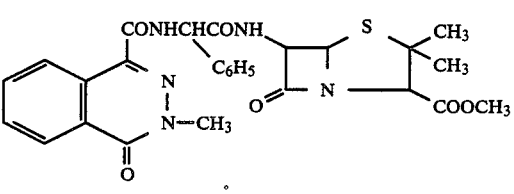 | | | | |
| 32 | Methyl ester of 6-[N—(2',4'-dimethyl-1'/2'H/—isoquinolinone-3'-carbonyl)-2R—2-aminophenylacetamido]-2,2-dimethyl-penam-3-carboxylic acid | 75 | 139–141 | (nujol) 1650-broad (CO,amide), 1730(CO,ester), 1790(CO,beta-lactam),3300(NH)<br>Calculated: N 9,96<br>Found: N 9,81<br>Calculated: S 5,69<br>Found: S 6,15 | $C_{29}H_{30}N_4O_6S$ (562,56) |

EXAMPLE 33

In the following table 4 is shown the activity of the compounds prepared according to the invention. Some of the anbiotics demonstrate a broad scope of action as seen in table 5. In both tables MIC signifies "Minimal growth inhibiting concentration."

TABLE 4

| EX-AMPLE | COMPOUND | MINIMAL INHIBITING CONCENTRATION (mkg/ml) STRAIN ||||||
|---|---|---|---|---|---|---|
| | | Ps. aeruginosa 2 | P. vulgaris 10 | Staph. aureus 31 | P. mirabilis 171 | E. coli II-0125 |
| 2 | [structure] | >100 | >100 | <12,5 | >100 | >100 |
| 3 | [structure] | >100 | >100 | <12,5 | >100 | >100 |
| 4 | [structure] | >100 | >100 | 12,5 | 100 | 50 |
| 8 | [structure] | 6,25 | >100 | <3,1 | <3,1 | <3,1 |
| 9 | [structure] | <12,5 | >100 | <12,5 | <12,5 | <12,5 |
| 5 | [structure] | >100 | <6,25 | >100 | >100 | >100 |
| 1 | [structure] | >100 | <6,25 | >100 | >100 | >100 |
| 6 | [structure] | >100 | <6,25 | >100 | >100 | >100 |

TABLE 4-continued

| EXAMPLE | COMPOUND | MINIMAL INHIBITING CONCENTRATION (mkg/ml) STRAIN | | | | |
|---|---|---|---|---|---|---|
| | | Ps. aeruginosa 2 | P. vulgaris 10 | Staph. aureus 31 | P. mirabilis 171 | E. coli II-0125 |
| 7 | [phthalazinone-penicillin structure with CONH, N-N-CH₃, S, CH₃, CH₃, COONa] | >100 | <6,25 | >100 | >100 | >100 |
| 10 | [isocoumarin structure with COOCH₃, CONHCHCONH, Ph, S, CH₃, CH₃, COONa] | <12,5 | >100 | <12,5 | <12,5 | <12,5 |
| 11 | [isocoumarin structure with CONHCHCONH, C₆H₅, S, CH₃, CH₃, COONa] | 100 | >100 | <3,1 | 6,25 | 25 |
| 12 | [structure with CONHCHCONH, C₆H₅, CH₃, S, CH₃, CH₃, COONa] | 100 | >100 | 100 | 100 | 25 |
| 13 | [isoquinolinone structure with CONHCHCONH, C₆H₅, N-CH₃, S, CH₃, CH₃, COONa] | 100 | >100 | 100 | >100 | 100 |
| 14 | [phthalazinone structure with CONHCHCONH, N, N-CH₃, S, CH₃, CH₃, COONa] | 50 | >100 | 12,5 | 12,5 | 2,5 |

TABLE 5

| EXAMPLE | COMPOUND | STRAIN MINIMAL INHIBITING CONCENTRATION (mkg/ml) | | | | | | | | | | | | |
|---|---|---|---|---|---|---|---|---|---|---|---|---|---|---|
| | | Ps. aeruginosa | | | | | Vl. pneumonia | | Entero-bacter | E. coli | | | P. mirabilis | | |
| | | 38 | 632 | 634 | 635 | 665 | 671 | 597 | 576 | 640 | 626 | 669 | 667 | 660 | 661 | 662 |
| 8 | (structure: 4-methylisocoumarin-3-carbonyl-NH-CH(C$_6$H$_5$)-CONH-penicillin Na) | 6,25 | | 6,25 | | | 25 | | | | | | | | | |
| 9 | (structure: 7,8-dimethoxyisocoumarin-3-carbonyl-NH-CH(C$_6$H$_5$)-CONH-penicillin Na) | | 6,25 | 6,25 | 25 | 25 | | 12,5 | 12,5 | 3,1 | 12,5 | 12,5 | 12,5 | 50 | 50 | 12,5 |
| 10 | (structure: 4-COOCH$_3$-isocoumarin-3-carbonyl-NH-CH(C$_6$H$_5$)-CONH-penicillin Na) | 12,5 | 12,5 | 25 | | | | | | 6,25 | 6,25 | 25 | 50 | >50 | 50 | 12,5 |

We claim:
1. Sodium salt of 6-[2'-methyl-1'(2'H)-isoquinolinone-4'-carboxylamide]-2,2-dimethyl-penam-3-carboxylic acid.
2. Sodium salt of 6-(2'-methyl-1'(2'H)-phthalazinone-4'-carboxylamide)-2,2-dimethyl-penam-3-carboxylic acid.
3. Sodium salt of 6-[N-(4'-methyl-isocumarine-3'-carbonyl)-2D-2-aminophenylacetamide]-2,2-dimethyl-penam-3-carboxylic acid wherein D is an aminophenyl acetamide moiety.
4. Sodium salt of 6-[N-(7',8'-dimethoxy-isocumarine-3'-carbonyl)-2D-2-aminophenylacetamide]-2,2-dimethyl-penam-3-carboxylic acid wherein D is an aminophenyl acetamide moiety.
5. Sodium salt of 6-[N-(4'-methoxycarbonyl-isocumarine-3'-carbonyl)-2D-2-aminophenylacetamide]-2,2-dimethyl-penam-3-carboxylic acid wherein D is an aminophenyl acetamide moiety.
6. Sodium salt of 6-[N-(isocumarine-4'carbonyl)-2D-2-aminophenylacetamide]-2,2-dimethyl-penam-3-carboxylic acid wherein D is an aminophenyl acetamide moiety.
7. Sodium salt of 6-[N-(3'-methyl-isocumarine-4'carbonyl)-2D-2-aminophenylacetamide]-2,2-dimethyl-penam-3-carboxylic acid wherein D is an aminophenyl acetamide moiety.
8. Sodium salt of 6-[-(24-methyl-1'(2'H)-isoquinolinone-4'-carbonyl)-2D-2-aminophenylacetamide]-2,2-dimethyl-penam-3-carboxylic acid wherein D is an aminophenyl acetamide moiety.
9. Sodium salt of 6-[N-(2'-methyl-1'(2'H)-phthalazinone-4'-carbonyl)-2D-2-aminophenylacetamide]-2,2-dimethyl-penam-3-carboxylic acid wherein D is an aminophenyl acetamide moiety.
10. Methyl ester of 6-[2'-methyl-1'(2'H)-isoquinolinone-4'-carboxamide]-2,2-dimethyl-penam-3-carboxylic acid.
11. Methyl ester of 6-[2'-methyl-1'(2'H)-phthalazinone-4'-carboxamide]-2,2-dimethyl-penam-3-carboxylic acid.
12. Methyl ester of 6-[N-(4'-methyl-isocumarine-3'-carbonyl)-2D-2-aminophenylacetamide]-2,2-dimethyl-penam-3-carboxylic acid wherein D is an aminophenyl acetamide moiety.
13. Methyl ester of 6-[N-(7',8'-dimethoxy-isocumarine-3'-carbonyl)-2D-2-aminophenylacetamide]-2,2-dimethyl-penam-3-carboxylic acid wherein D is an aminophenyl acetamide moiety.
14. Methyl ester of 6-[N-(4'-methoxycarbonyl-isocumarine-3'-carbonyl)-26-aminophenylacetamide]-2,2-dimethyl-penam-3-carboxylic acid.
15. Methyl ester of 6-[N-(isocumarine-4'-carbonyl)-2D-2-aminophenylacetamide]-2,2-dimethyl-penam-3-carboxylic acid wherein D is an aminophenyl acetamide moiety.
16. Methyl ester of 6-[N-(3'-methyl-isocumarine-4'-carbonyl)-2D-2-aminophenylacetamide]-2,2-dimethyl-penam-3-carboxylic acid wherein D is an aminophenyl acetamide moiety.
17. Methyl ester of 6-[N-(2'-methyl-1'(2'H)-isoquinolinone-4'-carbonyl)-2D-2-aminophenylacetamide]-2,2-dimethyl-penam-3-carboxylic acid wherein D is an aminophenyl acetamide moiety.
18. Methyl ester of 6-[N-(2'-methyl-1'(2'H)-phthalazinone-4'-carbonyl)-2D-2-aminophenylacetamide]-2,2-dimethyl-penam-3-carboxylic acid wherein D is an aminophenyl acetamide moiety.
19. Sodium salt of 6-[N-(2',4'-dimethyl-1'(2'H)-isoquinolinone-3'-carbonyl)-2D-2-aminophenylacetamide]-2,2-dimethyl-penam-3-carboxylic acid wherein D is an aminophenyl acetamide moiety.
20. Methyl ester of 6-[N-(2',4'-dimethyl-1'(2'H)-isoquinolinone-3'-carbonyl)-2D-2-aminophenylacetamide]-2,2-dimethyl-penam-3-carboxylic acid wherein D is an aminophenyl acetamide moiety.
21. Sodium salt of 6-[N-(4'-phenyl-isocumarine-3'-carbonyl)-2D-2-aminophenylacetamide]-2,2-dimethyl-penam-3-carboxylic acid wherein D is an aminophenyl acetamide moiety.
22. Sodium salt of 6-[N-(2'-methyl-4'-phenyl-1'(2'H)isoquinolinone-3'-carbonyl)-2D-2-aminophenylacetamide]-2,2-dimethyl-penam-3-carboxylic acid wherein D is an aminophenyl acetamide moiety.

* * * * *